(12) United States Patent
Fukushima et al.

(10) Patent No.: US 11,338,091 B2
(45) Date of Patent: May 24, 2022

(54) NEEDLELESS INJECTOR ASSEMBLIES AND RELATED METHODS

(71) Applicants: Masayoshi Fukushima, Orange, CA (US); Toshikazu Todo, Namerikawa (JP)

(72) Inventors: Masayoshi Fukushima, Orange, CA (US); Toshikazu Todo, Namerikawa (JP)

(73) Assignee: AIJEX PHARMA INTERNATIONAL INC., Toyama (JP)

( * ) Notice: Subject to any disclaimer, the term of this patent is extended or adjusted under 35 U.S.C. 154(b) by 0 days.

(21) Appl. No.: 16/762,789

(22) PCT Filed: Nov. 9, 2018

(86) PCT No.: PCT/US2018/060172
§ 371 (c)(1),
(2) Date: May 8, 2020

(87) PCT Pub. No.: WO2019/094827
PCT Pub. Date: May 16, 2019

(65) Prior Publication Data
US 2020/0316300 A1    Oct. 8, 2020

Related U.S. Application Data

(60) Provisional application No. 62/584,040, filed on Nov. 9, 2017.

(51) Int. Cl.
*A61M 5/30* (2006.01)

(52) U.S. Cl.
CPC ..................... *A61M 5/30* (2013.01)

(58) Field of Classification Search
CPC .. A61M 5/30; A61M 2005/2073; A61M 5/31; A61M 5/315
See application file for complete search history.

(56) References Cited

U.S. PATENT DOCUMENTS

| 5,569,189 A | 10/1996 | Parsons |
| 5,800,388 A * | 9/1998 | Schiff ...................... A61M 5/30 604/500 |

(Continued)

FOREIGN PATENT DOCUMENTS

| JP | 2005205168 A | 8/2005 |
| JP | 2016508402 A | 3/2016 |

(Continued)

OTHER PUBLICATIONS

International Search Report and Written Opinion on corresponding PCT application (PCT/US2018/060172) from International Searching Authority (US) dated Jan. 29, 2019.

(Continued)

*Primary Examiner* — Nathan R Price
*Assistant Examiner* — Melissa A Snyder
(74) *Attorney, Agent, or Firm* — Klein, O'Neill & Singh, LLP

(57) ABSTRACT

A needleless injector assembly can have a spring injector and an ampule. The spring injector can include a housing having a first housing portion and a second housing portion defining a bore and having a casing located in the bore and fixed relative to the first housing portion but the second housing portion can be rotatable relative to the casing. The casing can have a threaded receiving end at an end to threadedly receive a threaded end of an ampule. A pin having an end can project from the second housing portion and into an opening of the first housing portion and wherein the pin is retractable away from the first portion before the second housing portion is rotatable relative to the casing.

15 Claims, 10 Drawing Sheets

(56) References Cited

U.S. PATENT DOCUMENTS

| | | | |
|---|---|---|---|
| 7,547,293 B2 * | 6/2009 | Williamson | A61M 5/30 604/70 |
| 7,611,491 B2 | 11/2009 | Pickhard | |
| 8,679,071 B2 | 3/2014 | Hirschel et al. | |
| 2001/0051789 A1 | 12/2001 | Parsons | |
| 2005/0267403 A1 | 12/2005 | Landau et al. | |
| 2009/0157039 A1 | 6/2009 | Lenzner et al. | |
| 2010/0152659 A1 * | 6/2010 | Streit | A61M 5/2033 604/136 |

FOREIGN PATENT DOCUMENTS

| | | |
|---|---|---|
| WO | WO 2014/042930 A1 | 3/2014 |
| WO | WO 2014/187812 A1 | 11/2014 |

OTHER PUBLICATIONS

Notification of Reasons for Refusal on corresponding foreign application (JP Application No. 2020-544366) from the Japanese Patent Office dated May 11, 2021.

Extended European Search Reporton corresponding foreign application (EP Application No. 18875386.7) from the European Patent Office dated Jul. 8, 2021.

* cited by examiner

NEEDLELESS INJECTOR ASSEMBLIES AND RELATED METHODS

FIELD OF THE INVENTION

The present invention relates to needleless injector assemblies and more particularly to spring loaded injectors configured to expel fluid out a nozzle of an ampule.

BACKGROUND

A needleless hypodermic injector is a medical instrument that uses a high-pressure jet to expel a liquid medicament at a sufficient pressure and velocity to penetrate the skin and deposit the medicament under the skin, without a needle. The high pressure jet may be generated by forcing the liquid medicament through a sufficiently small nozzle at a sufficiently high rate of speed. To do so, a large force is typically applied to a plunger located in an ampule that causes the plunger to push the liquid towards the nozzle at an end of the ampule at a sufficiently high rate of speed to cause a volume of liquid ejected out through the nozzle with sufficient force to penetrate the epidermis of a recipient to a sufficient depth. Pressurized gas and/or mechanical device, such as a spring, may be used to generate the large force needed to push the plunger to then expel the liquid out of the ampule.

In needleless injector systems that use a spring, a compression spring with an appropriately sized spring constant is compressed to store potential energy and is held in a compressed state. To inject the liquid, the spring is released allowing the spring to rapidly expand to expel the stored energy. Typically, the spring is held in the compressed state by a latching mechanism. A trigger is then used to cause the latching mechanism to release the spring. The spring then decompresses within a housing having a piston and expels the piston to move the plunger located inside the ampule.

In re-useable needleless injector systems having a spring, the spring must be re-set to the compressed state after each use to then propel the plunger of a new or related ampule. To do so, the spring injector must be placed in a reloading system, such as a device for compressing and resetting the spring, that pushes the spring back into a compressed state and re-engages the latching system.

SUMMARY

An advance in the art is made by a safety system for a needleless injector assembly, or needleless injector for short, in accordance with various embodiments of the invention. A needleless hypodermic injector in accordance with some embodiments of this invention may include a housing that encloses a cavity. The housing can have a longitudinal axis with an injector opening on a first end of the housing along the longitudinal axis. A spring mechanism may be housed within the cavity proximate a second end of the body opposite the first end along the longitudinal axis. A piston within the cavity may abut the spring mechanism in the cavity between the spring and the first end. A latching mechanism may hold the piston in place in the cavity to, in turn, may hold the spring in a compressed state. The latching mechanism may be movable between a holding position and a firing position. The latching mechanism may be biased in the holding position to hold the piston in place in the cavity holding the spring in the compressed state and may move to the firing position in order to release the piston causing the spring to move from the compressed state to an uncompressed state within the cavity.

A trigger on an outer surface of the body may cooperate with the latching mechanism through an opening in the housing. The trigger can be movable between a ready position that allows the latching mechanism to be in the locking position and an action position that causes the latching mechanism to move to the firing position in order to release the piston and allow the spring to decompress. A safety with a nib protruding from a surface of the housing and may be movable between a locked position and an unlocked position. In the locked position, the nib prevents the trigger from moving between the ready and action positions. In the unlocked position, the nib is moved and allows the trigger to move from the ready position to the action position.

In accordance with some embodiments, the trigger includes a base having a top surface and a bottom surface. A first prong and a second prong may extend outwardly from the bottom surface of the base substantially parallel to one another and the longitudinal axis of the housing into the opening through the second end of the housing. Each of the first and second prongs may have a retaining member at a distal end of the prongs that cooperates with the latching mechanism. The latching mechanism then may include a body having a top and bottom surface.

A nib may protrude out of the top surface of the body to engage with the first and second prongs of the trigger and a shaft may extend out of the bottom surface of the body of the latching mechanism at a first end and affix to the piston on a second end. In accordance with some of these embodiments, the shaft may extend through the center of the spring from the bottom surface of the body on the first end to a top surface of the piston on the second end. In accordance with many of these embodiments, a lower inward facing side surface of the retaining member of each prong may be sloped and the sides of the nib may be outwardly sloped. An end cap of the nib may extend outward beyond the surface of a side surface of the nib to create an overhang. The overhang of the end cap rests upon the retaining members of the first and second prongs in response to the trigger being in the ready position to cause the latching mechanism to be held in the holding position.

In accordance with many of these embodiments, the trigger may move from the ready position to the action position by moving into the housing. The movement into the housing results in the retaining member of each prong being forced apart and releasing the end cap. The releasing of the end cap of the nib frees the piston that allows the spring to decompress.

In accordance with a number of embodiments, a pin may extend across the cavity in the housing proximate the opening in the second end housing and through an opening defined in the prongs of the trigger. The opening through the prongs of the trigger may be sized to allow the trigger to move between the ready and action positions and the pin forces portions of the prongs apart based on the movement of the trigger between the ready and action positions.

In accordance with a number of embodiments, the safety may include a covering surrounding an outer side surface of a casing in the housing. The covering may have a stable portion on a first end of the covering that is proximate the first end of the housing and a rotatable portion on a second end of the covering that is proximate the second end of the housing with the nib of the safety protruding out of a top of surface of the rotating portion. The rotating portion may rotatable about the casing to move from the locked position where the nib is engages with the trigger to the unlocked position where the nib is not engaged with the trigger.

In accordance with some of these embodiments, a nib may protrude out of the sidewall of the casing to engage a slot defined through a side of the rotatable portion of the covering to restrict the movement of the rotatable member between the locked and unlocked positions.

In accordance with many embodiments, the housing of the injector may have a recessed port defined in the first end of the casing that is configured to receive and couple to an ampule. The covering may have a bore defined through one side of the stable portion of the covering substantially parallel to the longitudinal axis of the housing with a first opening defined through a first end of the stable portion of the covering to the bore and a second opening defined in the second end of the stable portion of the covering to the bore. A shaft having a length that is substantially the same as a length of the stable portion of the covering may be inserted into the bore such that the shaft is movable between a loaded and an unloaded position. The shaft may biased into the unloaded position where an end of the shaft extends out of the first end of the stable portion of the covering over the recessed port in the casing and may move to the loaded position where a second end of the shaft in proximately even with a surface on the second end of the stable portion of the covering in response to an ampule being inserted into the cavity and coupled to the casing.

A pin may be held in a cavity in a first end of the rotatable portion of the covering. The pin may be biased in a first position within the cavity where a portion of the pin protrudes out of a surface of the first or inward facing end of the rotatable portion and may be movable to a second position where the pin is recessed within the cavity of the rotatable portion of the covering. When the shaft in the stable portion is in the unloaded position, the pin extends into the bore through second opening of the stable portion to hold the rotatable portion in place. When an ampule is inserted into the recessed port and coupled to the casing, the shaft moves to the loaded position, the movement by the shaft dislodges the pin from the opening and moves the pin to the recessed position within the rotatable portion of the covering allowing the rotatable portion to move.

In accordance with many of these embodiments, the base of the trigger may have an elongated portion that extends out of the casing over the covering. The elongated portion may be engaged by the nib of the rotating portion when the safety is in the locked position and is free to move towards the body when the nib is moved by the rotatable portion being in the unlocked position.

A further aspect of the invention is a needleless injector assembly comprising: a spring injector comprising a housing having a first housing portion and a second housing portion defining a bore that is common to the first housing portion and the second housing portion; a casing is located in the bore and is fixed relative to the first housing portion but the second housing portion is rotatable relative to the casing; a threaded receiving end at an end of the casing to threadedly receive a threaded end of an ampule; a pin having an end projecting from the second housing portion and into an opening of the first housing portion; and wherein the pin is retractable away from the first portion before the second housing portion is rotatable relative to the casing.

The second housing portion can be rotatable relative to the first housing portion.

The pin can be located in a bore of a base portion of the second housing portion.

A shaft can be located in a bore of the first housing portion. The shaft can move against the pin to push the pin to not project into the opening of the first housing portion.

The shaft can be moved by an ampule to move against the pin.

A trigger can be pushed when the trigger is aligned to fit within a width of two nibs.

The trigger can be aligned with the second housing portion is rotated relative to the first housing portion.

The ampule can have male threads and can be threaded to into female threads at the threaded receiving end of the casing.

A piston and a spring can be located inside the casing.

A trigger having a push end can be located externally of the second housing portion and a triggering mechanism comprising two relatively movable prongs can be provided with the trigger.

The piston can comprise a piston head and a shaft having a latching body.

The trigger can have a push end located externally of the second housing portion and a triggering mechanism comprising two relatively movable prongs each comprising retaining member that grips the latching body to hold the spring in a compressed state.

A slit can pass between the two prongs and an opening formed by two cut-outs can be provided between the two prongs.

A still further aspect of the invention is a method of making a needleless injector assembly comprising: forming a spring injector comprising a housing having a first housing portion and a second housing portion defining a bore that is common to the first housing portion and the second housing portion; placing a casing in the bore so that the casing is fixed relative to the first housing portion but the second housing portion is rotatable relative to the casing; providing the casing with a threaded receiving end at an end of the casing to threadedly receive a threaded end of an ampule; placing a pin having an end projecting from the second housing portion and into an opening of the first housing portion; and wherein the pin is retractable away from the first portion before the second housing portion is rotatable relative to the casing.

The method can further comprise placing a shaft in a bore of a base portion of the first housing portion.

The method can further comprise attaching an ampule to the casing so that the ampule pushes the shaft into the pin.

The method can further comprise providing a trigger having two movable prongs, a piston, and a spring and gripping the piston with the two movable prongs.

The method can further comprise rotating the second housing portion relative to the first housing portion.

The method can further comprise moving the trigger after the second housing portion is rotated.

Methods of making and of using the needleless hypodermic injector and components thereof, including spring injectors and ampules, are within the scope of the present invention

BRIEF DESCRIPTION OF THE FIGURES

These and other features and advantages of the present devices, systems, and methods will become appreciated as the same becomes better understood with reference to the specification, claims and appended drawings wherein:

DETAILED DESCRIPTION

Figure 1:
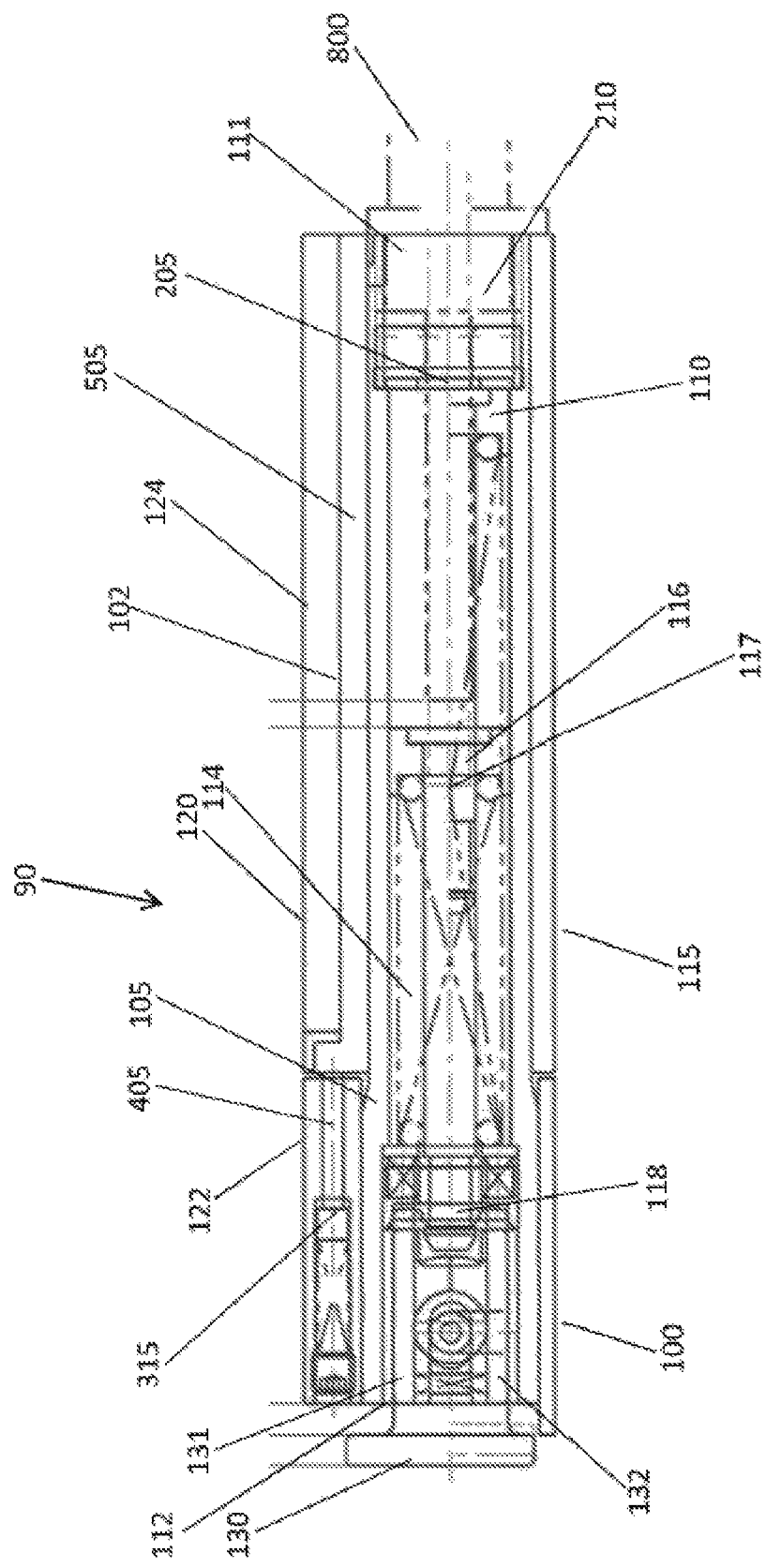
FIG. 1 illustrates a partial side cross sectional view of a needleless injector assembly comprising a spring ejector coupled to an ampule in in accordance with an embodiment of the invention.

The detailed description set forth below in connection with the appended drawings is intended as a description of the presently preferred embodiments of needleless injectors and components thereof provided in accordance with aspects of the present devices, systems, and methods and is not intended to represent the only forms in which the present devices, systems, and methods may be constructed or utilized. The description sets forth the features and the steps for constructing and using the embodiments of the present devices, systems, and methods in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features.

Needleless injectors are disclosed in which an exemplary needleless injector can include a spring injector and an ampule. Broadly speaking, the spring injector is a motive supply source for supplying the needed energy to propel the plunger inside the ampule. The spring injector can have a housing having a spring and a piston, to be propelled by the spring, located inside the housing. The ampule can comprise a body shaped as a barrel having a discharge nozzle located at one end and an opening receiving a plunger in a sliding arrangement to displace fluid held inside the barrel out through the nozzle.

The coiled spring of the spring injector can be held in a compressed state after being loaded or set by a releasable latching mechanism. A safety system can be incorporated with the spring injector to prevent the latching mechanism from releasing. An exemplary safety system in accordance with aspects of the invention is described below. The safety system can prevent a trigger of the latching mechanism from moving to fire the spring injector, such as to release the spring. In accordance with some embodiments, the trigger is located on or positioned to a back or end section of the housing of the injector, remote from the ampule. The trigger is movable, such as by the urging of digital pressure, to activate a latching mechanism to release the spring or other force providing mechanism. In other examples, the trigger can be located elsewhere on the spring injector.

As further discussed below, the trigger can slide, displace, or move into the housing to activate the latch mechanism and the safety system is configured to prevent movement of the trigger into the housing unless or until the safety system is turned off or deactivated. In some examples, the rigger can be pivotably mounted and the act of trigging causes the trigger to pivot.

In accordance with some of these embodiments, the housing of the spring injector defines an enclosed space having a spring and a piston disposed therein. The trigger can have an overhang portion of an exposed portion of a base that extends over a portion of a back or bottom surface of the housing. The housing can have a nib that protrudes from the back or bottom surface of a rotating portion of the housing that is under the overhanging portion of the trigger to restrict movement of the trigger into the housing of the injector. A nib can be an end portion of a part or structure. To fire the injector, the nib is moved to position away from the overhanging portion of the trigger where the nib is no longer in contact with the overhanging portion of the trigger. In accordance with some of these embodiments, the nib is moved by rotating the rotatable portion of the housing to move the nib to position where the nib does not block movement of the overhanging portion of the trigger.

In accordance with some embodiments of the invention, the safety system can prevent or resist premature triggering of the trigger when an ampule is not engaged with the injector. Having this safety feature can reduce the risk of a misfire during a reloading of the injector. In accordance with some of these embodiments, the safety system prevents the nib from being moved from under the overhanging portion of the trigger when an ampule is not engaged. In accordance with many of these embodiments, the nib is prevented from moving by securing the rotating portion of the housing in place when an ampule is not coupled to the injector. In accordance with a number of these embodiments, the rotating portion of the housing has a movable pin that is housed by a cavity in a first or inward facing surface of the rotating portion. The pin can be biased to a position where at least a portion of the pin protrudes out of the inward facing surface of the rotating portion.

A stable portion of the housing has a movable shaft in a bore through the stable portion. The shaft may be approximately the same length as the stable portion and can be biased to extend out of a first or outward facing surface of the stable portion creating a recessed area in the bore on a second or inward facing surface of the stable portion. The pin from the rotating portion can extend into the recessed area of the stable portion to restrict movement of the rotating portion. When an ampule is coupled to the injector, the ampule can push against the shaft causing the shaft to move to the loaded position where a second end of the shaft is flush with the second or inward facing surface of the stable portion. The movement of the shaft pushes the pin of the rotating member back into the cavity in the rotating member allowing the rotating member to rotate. The pin may be kept in the cavity by abutting against the second or inward facing surface of the stable member as the rotating portion rotates.

In accordance with some embodiments, the rotation of the rotating portion may be restricted to allow the rotating portion to only rotate between a locked and unlocked position. In accordance with some of these embodiments, a nib extends outward from an inside of the housing to cooperate with a groove on through a side surface of the rotating portion of the housing to restrict the rotation to of the rotating portion.

In accordance with many embodiments, the movement of the trigger may be restricted to allow the trigger to only move between a ready position and a firing position. In accordance with a number of embodiments, the movement is restricted by a pin that extends across the cavity of the housing through an opening in the base of the trigger to allow the trigger to only move the length of the opening. Furthermore, the pin may have a side that is designed to press against prongs of the trigger forcing the prongs to open and release a latch in accordance with many embodiments of the invention.

The above and other advantages of a safety system of a needleless hypodermic injector in accordance with some embodiments of the invention are described below with reference to the drawings.

Figure 10:
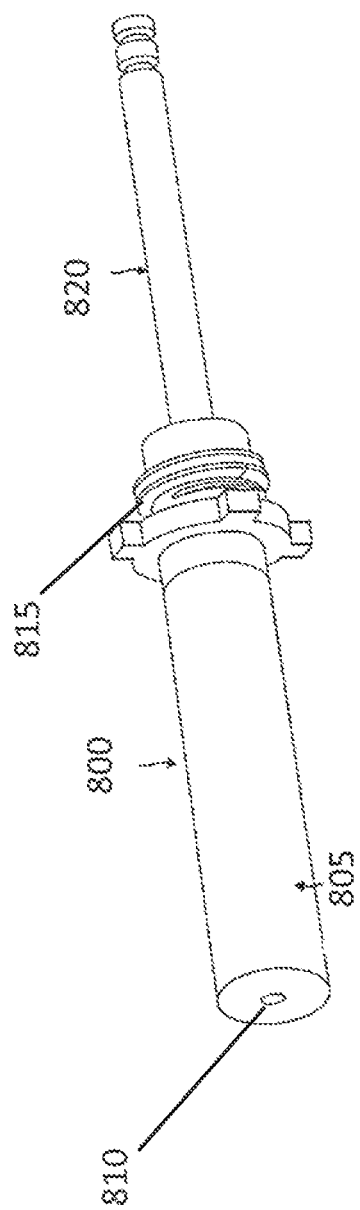
FIG. 10 illustrates an ampule with a plunger for use with a spring injector to form a needless injector assembly in accordance with an embodiment of the invention.

A needleless injector 90 in accordance with an embodiment of the invention includes a spring injector 100 and an ampule 800 (FIG. 10). Exemplary ampules are disclosed in PCT publication No. WO 2014/042930 and No. WO 2017/176910, the contents of which are expressly incorporated herein by reference. A spring injector 100 in accordance with an embodiment of the invention is shown in FIGS. 1-4. Each of FIGS. 1-4 shows a partial cross sectional views of the spring injector, which is generally designated 100. The spring injector 100 has a housing 102. Housing 102 includes a casing 105 and a covering 120. In accordance with some other embodiments, casing 105 and covering 120 are integral to another, can be secured to one another, or can be assembled to one another. In accordance with many other embodiments, casing 105 may only include end caps inserted into opposing ends of covering 120. In the shown embodiment, casing 105 is made from a metallic material and has an elongated body with a longitudinal axis. In accordance with some other embodiments, casing 105 may be made from a plastic and in accordance with various other embodiments may be made of any other material that can contain the force applied when a spring or other force applying component is activated.

Casing 105 has a wall surface defining a cavity 110 that has an injector opening 111 through a first end of the casing 105 along the longitudinal axis. A spring 114 is housed or disposed within cavity 110 proximate a second or cap end of casing 105 opposite the first end along the longitudinal axis. In accordance with some embodiments, the spring is a compression spring capable of storing enough energy to impart a force sufficient to drive a liquid medicament out of the nozzle at a sufficient rate to generate the desired force to penetrate the epidermis of a patient to a desired depth. In accordance with some other embodiments, a pressurized gas in a gas canister may be used to provide the force. A piston head 116 within the cavity 110 has one surface abutting spring 114 in cavity 110 between spring 114 of the first end of casing 105 and a second end abutting a shaft 119 of a plunger of an ampule (Shown in FIG. 8).

Shaft 119 extends through an injector opening 205 into a recessed coupling 210 that is a cavity defined in the injector end of casing 105 to couple to an ampule. In accordance with some embodiments, the recessed coupling 210 may include threading mated to threading on a sidewall of an ampule for coupling the ampule to casing 105. In accordance with a number of embodiments where casing 105 and covering 120 are integral to one another, recessed coupling may be a metallic cap inserted into an opening of covering 120.

Piston head 116 is held in place in cavity 110 by a latching mechanism to hold spring 114 in a compressed state. When piston head 116 is released by the latching mechanism, piston head 116 is free to move within cavity 105. The freedom of movement of piston head 116 allows spring 114 to decompress or expand from a compressed state. The decompressing spring pushes piston head 116 towards the injector end of the cavity 105 causing piston head 116 to push on shaft 119. Shaft 119 pushes the plunger in the ampule towards a nozzle in an injector end of the ampule. The movement of the plunger into the ampule forces liquid medicament in the ampule to be expelled out the nozzle. A more complete description of the operation of an needleless injector is provided in U.S. Pat. No. 6,913,592, which is hereby incorporated by reference as if set forth in its entirety herewith.

In accordance with many embodiments of the invention, a latching mechanism is movable between a holding position and a firing position. In the holding position, the latching mechanism holds piston head 116 in place in cavity 110 to hold spring 114 in a compressed state. For example, the piston head 116 can have a shaft and a piston head. The spring can surround the shaft and abut against the piston head. The piston head can move to compress the spring and the spring can be held in the holding position by prevent the piston, such as the piston head, from moving in the opposite direction. In the firing position, the latching mechanism allows piston head 116 to move. When piston head 116 is freed to move, spring 114 may decompress to release the energy stored during compression.

In FIGS. 1-4, the latch mechanism is provided by a latch body 118 and part of an ampule is shown schematically at the attachment end. Latch body 118 has a top surface and a bottom surface, or first and second surfaces. The bottom surface of latch body 118 is connected to one end of a shaft 117. The second end of shaft 117 is connected to piston head 116. A piston 115 used herein has a shaft 117 and a piston head 116. A nib 160 protrudes out of the top surface of latch body 118 to engage with the first and second prongs 131, 132 of a trigger 130. The trigger 130 can have a push end 712 (FIG. 9A), or a structure that a user can manipulate to push the trigger, and a triggering mechanism 133, which can comprise the first and second prongs 131, 132. In the shown embodiment, shaft 117 extends through the interior of the coils of spring 114. However, the shaft may be external to spring 114 in accordance with some other embodiments. A description of the operation of the latching body is provided below in relation to FIGS. 7A-7D.

Although a latching mechanism in accordance with an embodiment of the invention is described above, other latching mechanisms having other configurations based upon the configuration of various other components of a needleless injector are possible in accordance with various other embodiments of the invention.

Returning to FIG. 1, a trigger 130 having a push end on an outer surface of housing 102 cooperates with the latching mechanism through an opening 112 in housing 102. In accordance with some embodiments, trigger 130 is metallic. In accordance with many other embodiments, trigger 130 is plastic. In accordance with a number of other embodiments, trigger 130 is made of any other material or combination of materials that is capable of withstanding the various forces applied to trigger 130. Trigger 130 is movable between a ready position and an action position. In the ready position, trigger 130 holds or maintains the latching mechanism in the locking position. In the action position, trigger, when pressed, allows and/or causes the latching mechanism to move to the firing position that, in turn, releases the piston 115, such as the piston head 116, allowing spring 114 to decompress.

In the shown embodiment, trigger 130 includes a base having a top surface and a bottom surface. A first prong 131 and a second prong 132 extend outwardly from the bottom surface of trigger 130 substantially parallel to one another and to the longitudinal axis of housing 102 into an opening 112 through a cap end of housing 102. Each of the first and second prongs 131, 132 has a retaining member at a distal end of the prong that cooperates with the latching body 118. Furthermore, each of prongs 131, 132 has a split defined between opposing portions between opening 705 and a distal end of the prongs that allows the portions to separate in response to a force applied by pin 710 as discussed in further detail below.

In accordance with the embodiment shown in FIG. 1, the retaining members of first and second prongs 131, 132 hold latch body 218 in place within cavity 105. Trigger 130 moves from the ready position to action position by being pushed in the direction into opening 112. The movement of trigger 130 into the opening causes first and second prongs 131, 132 to spread apart from one another. In accordance with some embodiments, the spreading apart of the prongs is caused by pin 710 that extends through an opening 705 through each of the prongs.

In an example, pin 710 is shaped such that pin 710 pushes against side walls of the openings 705 forcing opposing portions of the prongs apart as the trigger travels into cavity 110. The spreading of the portions of prongs 131, 132 into the action position causes the retaining members of the prongs to release latch body 118. The release of the latch body 118 causes the latch body 118 to be in a firing position where latch body 118 is free of the retaining members of prongs 131, 132. This frees the piston head 116 to move, in turn, allowing spring 114 to decompress. A more detailed discussion of the prongs and the operation of trigger 130 is provided below with reference to FIGS. 9A-9D. In some examples, the trigger has a push end or head end and an activation end. The activation end can push a cam to cause the prongs 131, 132 to spread or move away from one another to release the piston 115. Thus, aspects of the invention is understood to include a trigger having a push end configured to be pushed by a user and an activation end and wherein the activation end moves to push a pin, a cam, or other structural features to move the prongs 131, 132 away from one another to release the piston to then allow the spring to decompress or expand from a compressed state.

A trigger on an end cap of a spring injector in accordance with an embodiment of the invention is described above. However, other triggers that are located elsewhere on the housing and that operate in other manners based upon the configuration of components in various other needleless injectors in accordance with various other embodiments of the invention are possible.

In accordance with some embodiments of the invention, a safety is coupled to an outer surface of housing 102. The safety is movable between a locked position and an unlocked position. In the locked position, the safety restricts the movement of trigger 130 between the ready position and the action position. In accordance with some embodiments, the safety has a nib protruding from a surface of the safety or from the rotatable housing. The nib can prevent the trigger from moving between the ready and action positions by acting as a physical barrier to block the movement of the trigger. When the safety moves from the locked position to the unlocked position, the nib is positioned relative to the trigger to allow the trigger to move from the ready position to the action position. In some examples, two nibs are provided and the two nibs define a gap therebetween. When the safety is activated, the nibs and the trigger positioned so that the width of the trigger fits between the gap defined by the two nibs to allow the trigger to move from the ready position to the action position. The operation of the safety in accordance with some embodiments of the invention is discussed below with reference to FIGS. 5-8.

In the embodiment shown in FIG. 1, the safety is provided by covering 120, which can embody an elongated structure having a bore. Covering 120 surrounds an outer surface of casing 105 and casing 105 is located in the bore of the covering 120, which acts as a housing for the casing 105. In the shown embodiment covering 120 is plastic. However, covering 120 may be made of any other material that meets design and/or functional requirements of various other embodiments of the invention.

In an example, the covering or housing 120 has a front or first housing portion 124, which can be stable portion that does not rotate and is held fixed relative to the casing 105, and a rear or second housing portion 122, which can be a rotatable portion 122 proximate the cap end of casing 105. Nibs 350 (FIG. 3) can protrude out of an outer end surface of a cap end of rotating portion 122.

In an example, there can be two nibs 350. The push end of the trigger can have a non-circular shape. For example, the push end can have an elongated oval shape like a track around a football field. The elongated oval shape has two different dimensions along the length and width. The two nibs can define a gap therebetween. In an example, the trigger 130 has a push end having a width, such as the long dimension, that is larger than the gap defined by the two nibs 350. However, when the rotatable portion 122 is rotated, the shorter dimension of the push end of the trigger is now aligned with the gap defined by the two nibs and can be pushed to pass between the two nibs to activate the spring.

Figure 3:
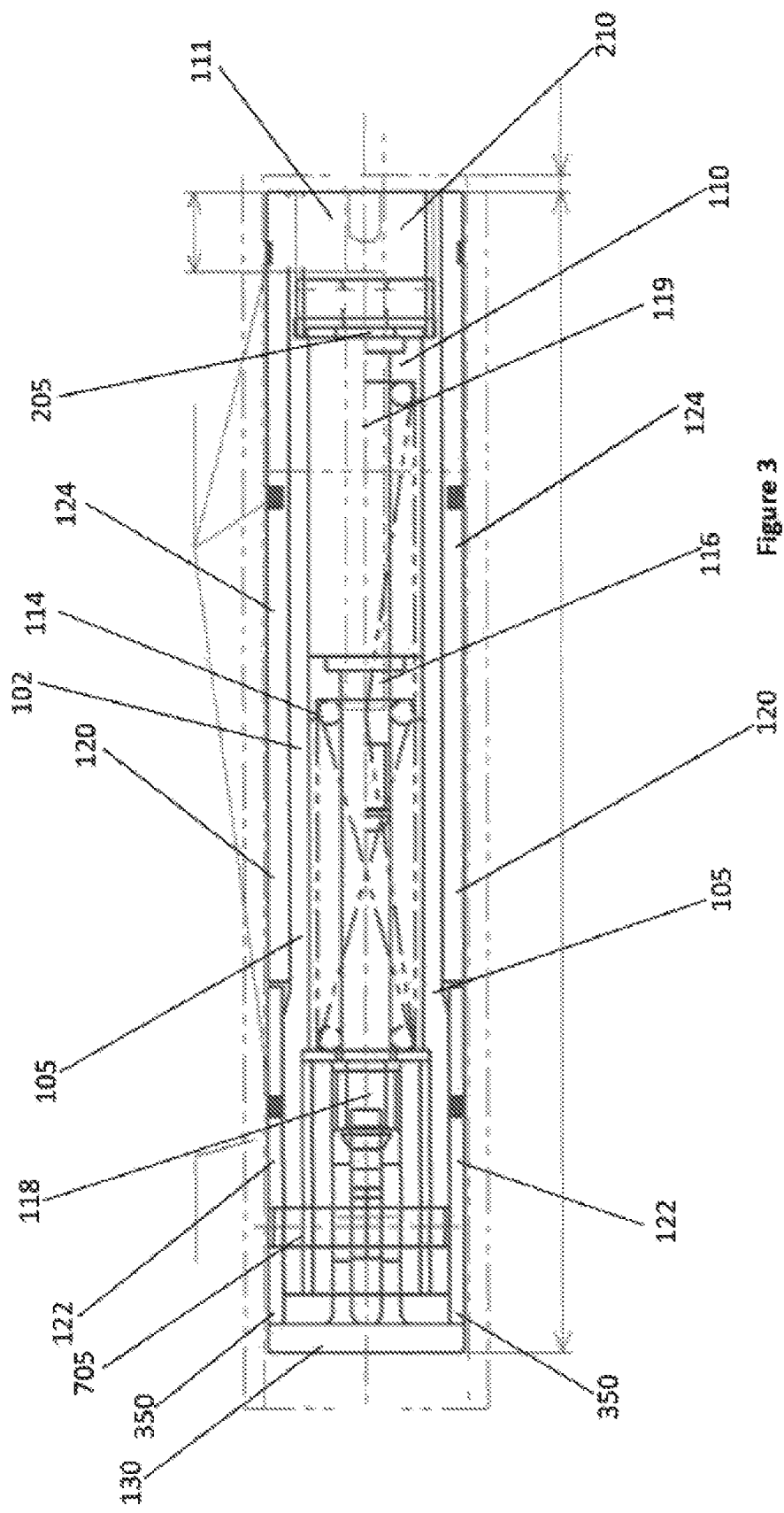
FIG. 3 illustrates a partial top side cross sectional view of the spring ejector in accordance with the embodiment shown in FIG. 1.
Figure 4:
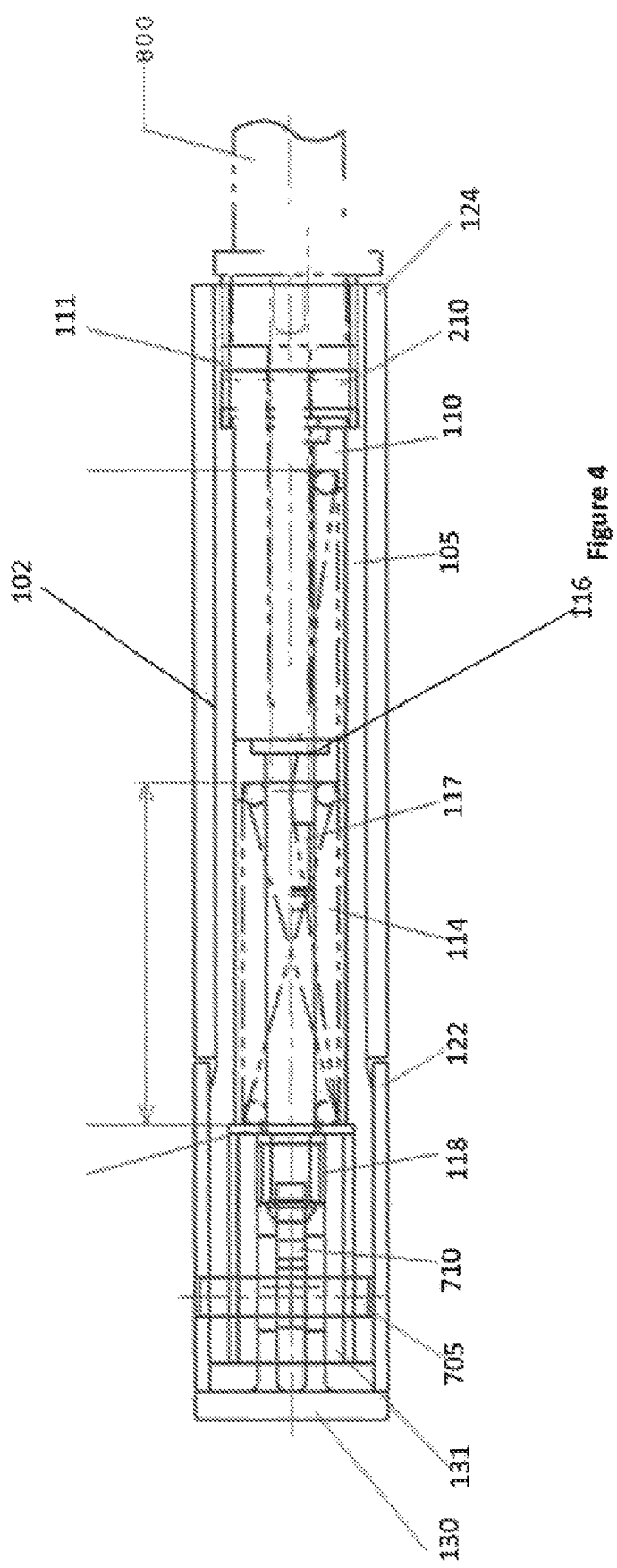
FIG. 4 illustrates a partial top side cross sectional view of spring ejector coupled from an ampule in accordance with the embodiment shown in FIG. 1.

Rotating portion 122 is rotatable about casing 105 to move from the locked position to the unlocked position. In the locked position, the nibs 350 engage trigger 130 to block trigger 130 from being pushed into casing 105 through opening 112. In the unlocked position, the nib is positioned such that trigger 130 is not engaged by the nibs 350 and trigger 130 may be moved into opening 112, as discussed immediately above. A more complete description of casing 120 and its operation is discussed below with reference to FIGS. 5-8 where FIG. 3 is an exploded view of casing 120 in accordance with an embodiment of the invention; FIG. 4 is an end view of a first or inward surface of the rotating portion in accordance with an embodiment of the invention; and FIG. 5 is an end view of a f end of stable portion 124.

Figure 5:
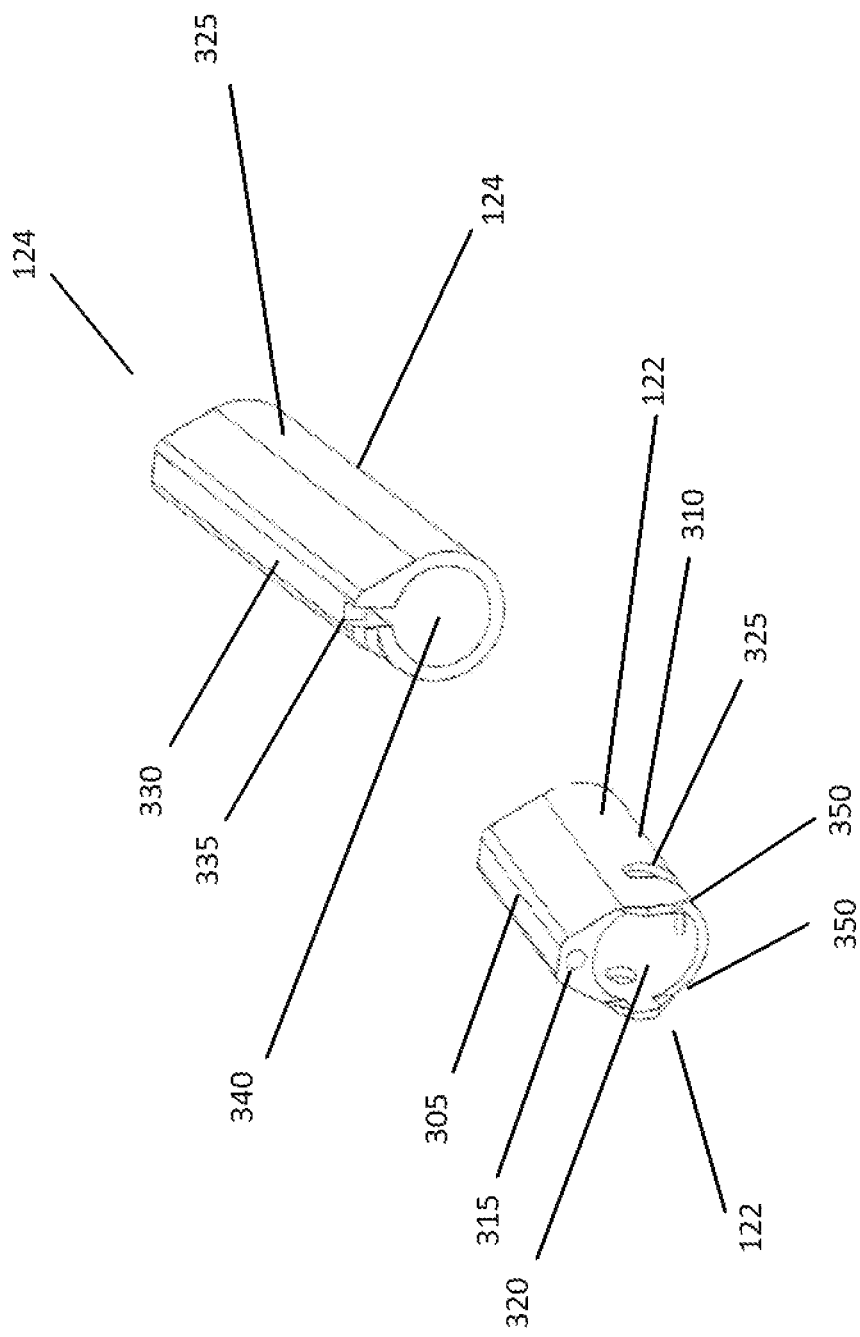
FIG. 5 illustrates a perspective view of a housing of a spring injector of a needleless injector in accordance with an embodiment of the invention, which has a first housing portion and a second housing portion.

In FIGS. 3-5, covering 120 includes rotating portion 122 and a stable portion 124 as previously presented. In an example and when assembled, the casing 105 is located in both the rotating portion 122 and the stable portion 124. However, only the rotating portion 122 is rotatable relative to the both the stable portion and the casing 105 while the stable portion is fixed relative to the casing. The rotating portion 122 has a substantially cylindrical portion 310 and a base portion 305. Substantially cylindrical portion 310 has an opening 320 through which casing 105 (Shown in FIGS. 1-4) is inserted to allow portion 310 to enclose casing 105. In accordance with some embodiments, only a metallic end cap for coupling to the trigger is inserted through rotating portion 122 and into the first or inward facing end of stable portion 124. Opening 320 is sized and shaped to be tight enough to hold rotating portion in place on casing 105 and large enough to allow rotating portion 122 to slide over casing 105 to rotate substantially about the longitudinal axis of casing 105. In accordance with some other embodiments, rotating portion 122 may slide substantially back and forth along longitudinal axis over casing 105 substantially parallel to the longitudinal axis.

A groove 325 is defined in substantially cylindrical portion 310 in a direction of rotation. Groove 325 cooperates with a nib 610 (Shown in FIG. 8) that protrudes from a sidewall of casing 105 to restrict the distance that rotating portion 122 may rotate about casing 105. In accordance with some embodiments, the ends of groove 325 define the locked and unlocked positions of rotating member 122. Nibs 350 protrude out of opposing sides of the top surface of substantially cylindrical portion 310. Nibs 350 engage the trigger when the safety is in the locked position to restrict the movement of trigger 130 into cavity 110 of casing 105 as is discussed in more detail below. Although two nibs 350 are shown, there may be any number of nibs that project out of the top surface and/or sidewall of substantially cylindrical portion 310 to engage trigger 130 when the safety is in the locked position.

Base portion 305 protrudes out of one side substantially cylindrical portion 310. A pin 405 is housed in a bore 315 in base portion 305. The bore 315 can have an opening on an internal surface of base portion 305 that faces an internal surface of base portion 330 of stable portion 124. Pin 405 is movable between an exposed position (Shown in FIG. 1) and a recessed position (Shown in FIG. 2). In the exposed position, pin 405 protrudes out of bore 315 past the inward facing surface of base portion 305 and in the bore, pin 405 is enclosed in the bore 315 with a top portion of the pin at or below the internal surface. In accordance with some embodiments, pin 405 is biased in the exposed position. In accordance with some of these embodiments, pin 405 is biased in the exposed position by a spring inside cavity 315. In the pin exposed position, the ampule is not connected to the spring injector. In the pin recessed position, the pin is moved by a shaft 505 that is moved by the ampule. The ampule causes the shaft to move which then pushes the pin 405 to locate inside or recessed inside the rotating portion. In an example, the location of the pin 405 acts as a safety mechanism to prevent the rotating portion 122 from rotating relative to the stable portion 124. When the rotating portion 122 cannot rotate from a locked position to an unlocked position. This in turn prevents the push end of the trigger from being pushed to release the spring.

Thus, an aspect of the invention is a safety feature that has at least two independently movable steps. In an example, the safety feature has a first step that involves moving a pin 405 from an exposed positioned to a position inside a housing section. Movement of said pin causes a nib or an end of the pin to recess or move away from the stable portion 124 and into the rotating portion 122. The safety feature can comprise a second step before the trigger can be activated. In an example, the safety feature comprises moving the rotatable portion 122 relative to the stable portion 124. In an example, rotation of the rotatable portion relative to the stable portion can only occur after movement of the pin 405. In exemplary embodiments, rotation of the rotatable portion 122 moves at least one nib 350 on the rotatable portion 122 so that the at least one nib does not physically obstruct the path of the push end of the trigger. As discussed above, there can be two nibs 350 defining a gap and rotation of the rotatable portion can allow the push end of the trigger to travel between the gap defined by the two nibs 350.

The stable portion 124 of housing 120 has a substantially cylindrical portion 325 and a base portion 330. Substantially cylindrical portion 325 has an opening 340 through which casing 105 (Shown in FIGS. 1 and 2) is inserted to allow portion 325 to enclose casing 105. Opening 340 is sized and shaped to be tight enough to hold stable portion 124 in place on casing 105. In accordance with some embodiments, stable portion 124 may have a greater length than rotating portion 122. Base portion 330 has a bore 335 with an opening formed through the base portion 330 and is aligned substantially parallel to the longitudinal axis. Bore 335 has a first opening and second opening on the opposing ends of stable portion 122. The first opening is defined through an inward facing surface of stable portion 124 that faces the inward facing surface of rotating portion 122 and the second opening is defined through an injector end surface of stable portion 122 proximate the injector end of housing 120.

Figure 2:
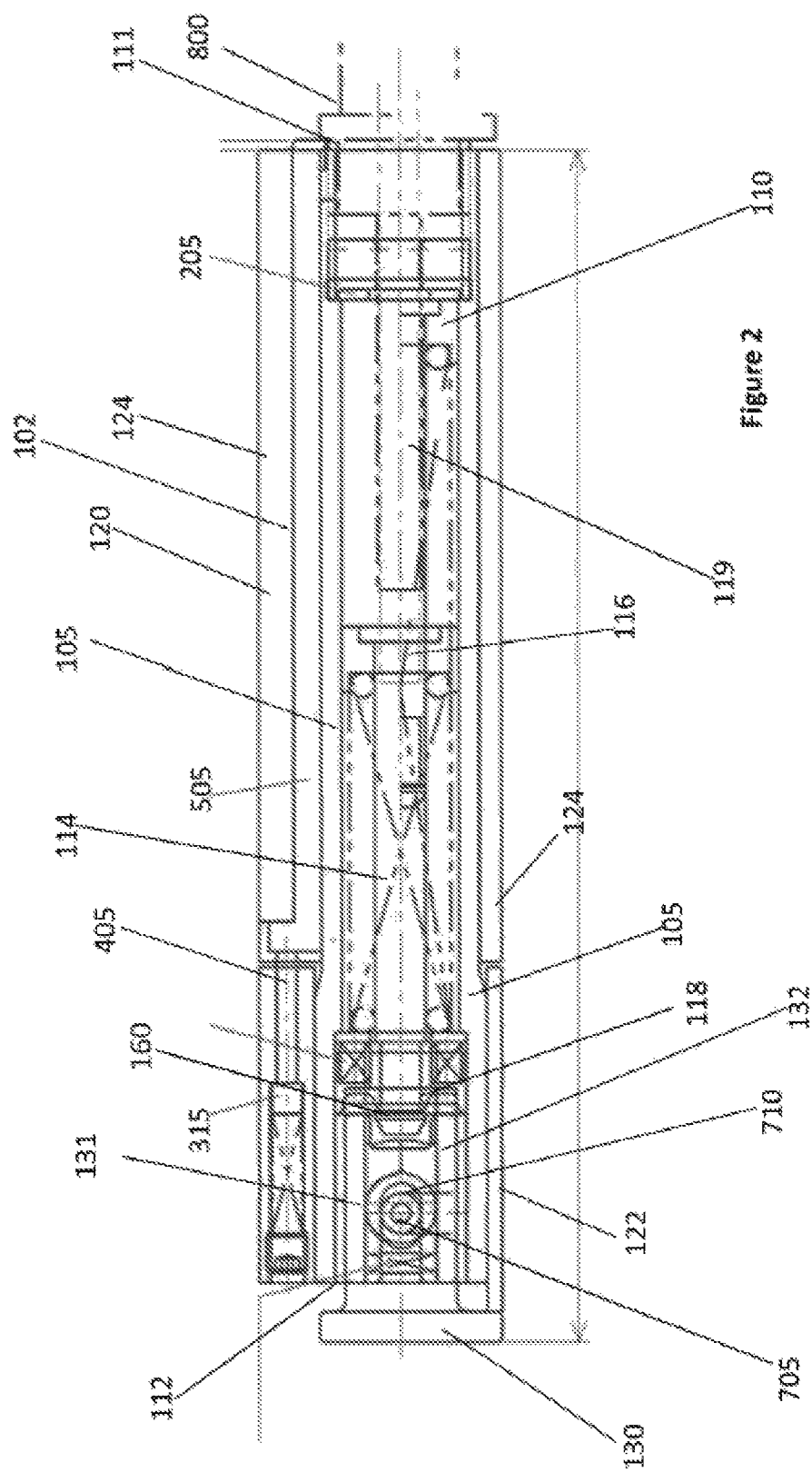
FIG. 2 illustrates a partial side cross sectional view of the spring ejector in accordance with the embodiment shown in FIG. 1.

A shaft 505 (FIG. 2) can have about the same length as the stable portion 124 and is inserted into bore 335 (FIG. 5) of the stable portion. Shaft 505 has an end that projects outward of the stable portion 124 near the connection end with the housing (FIG. 2). This extended part of the shaft 505 can be pushed by the ampule to cause the shaft to move against the pin 305 to push the tip of the pin away from the stable portion 124. Thus, the shaft 505 is movable between a loaded and unloaded position. In the unloaded position, a first end of the shaft 505 extends out of the injector end of the stable portion 124 over the ampule coupling 210 in the injector end of the casing 105 and a second end is recessed into bore 335.

In the loaded position, the first end of shaft 505 is proximately even with the injector end or outward facing surface of stable portion 124 and the second end of the shaft is proximately even with the inwardly facing surface of stable portion 124. In the unloaded position, pin 405 is in the exposed position and may extend into the bore 335 to cooperate with pin 405 to prevent the rotating portion 122 from moving or rotating relative to the stable portion 124. In the loaded position, pin 405 is pushed out of bore 335 and into the recessed position inside the bore 315 of rotating portion 122 allowing rotating portion 122 to rotate about casing 105. In accordance with some embodiments, shaft 505 is biased into the unloaded position by a spring or other biasing device in the bore 335. In accordance with the shown embodiment, shaft 505 is pushed from the unloaded position to the loaded position by an ampule being inserted into and coupled with housing 102.

Figure 6:
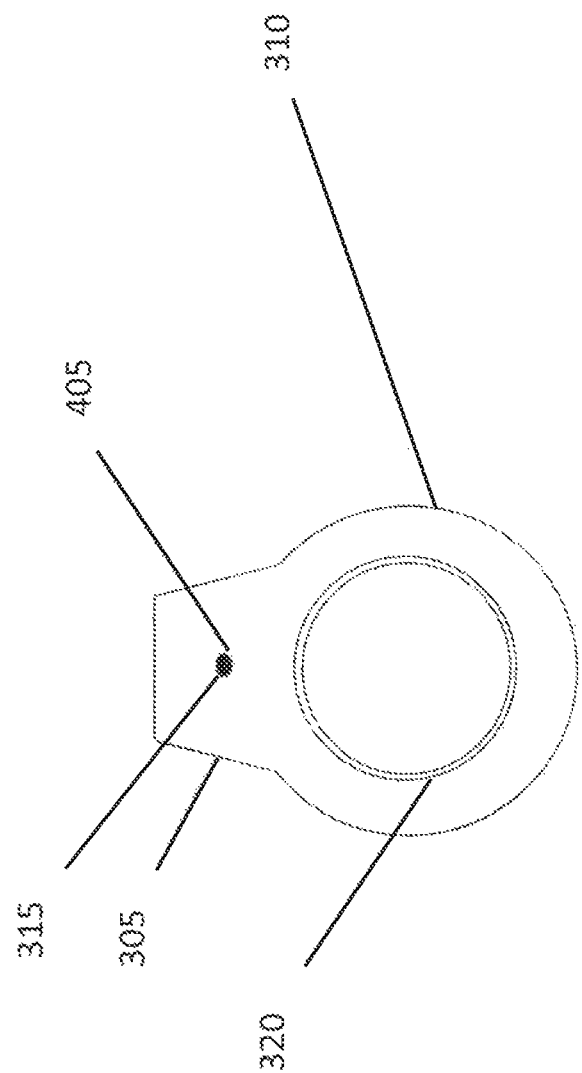
FIG. 6 illustrates an end view of a rotatable portion or second housing portion of the housing of the spring injector shown in FIG. 3.
Figure 7:
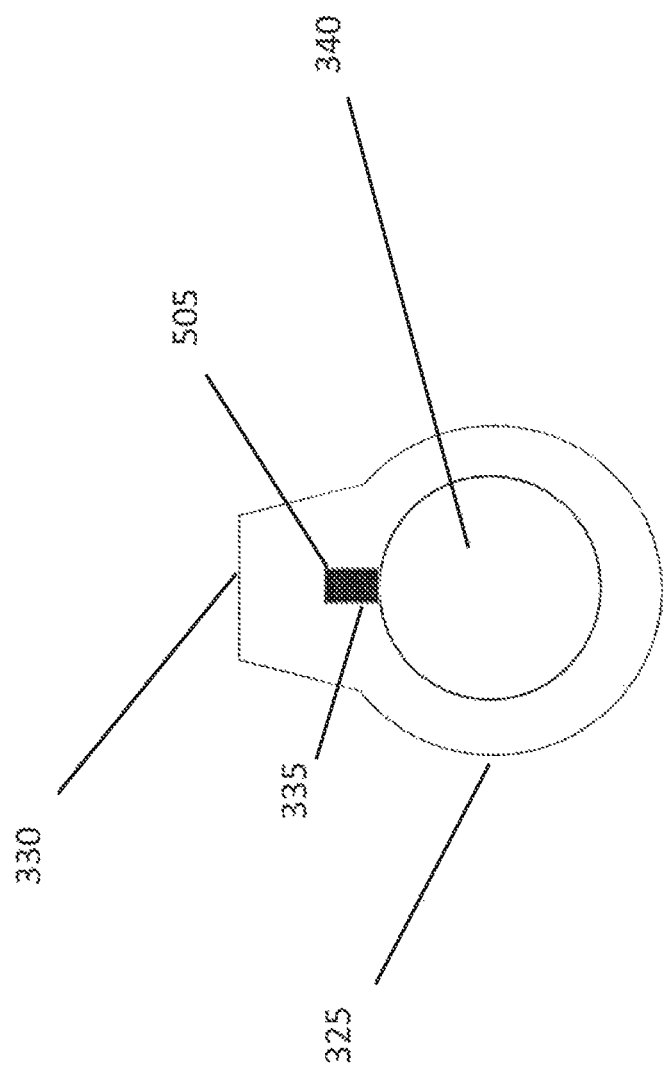
FIG. 7 illustrates an end view of a stable portion or first housing portion of the housing shown in FIG. 3.

Although casing providing a safety in accordance with an embodiment of the invention is described with reference to FIGS. 5-7, other casings providing the safety in other manners that add, combine, modify and/or remove components based on the configuration and requirements of particular needleless injectors in accordance with various other embodiments of the invention are possible.

Figure 8:
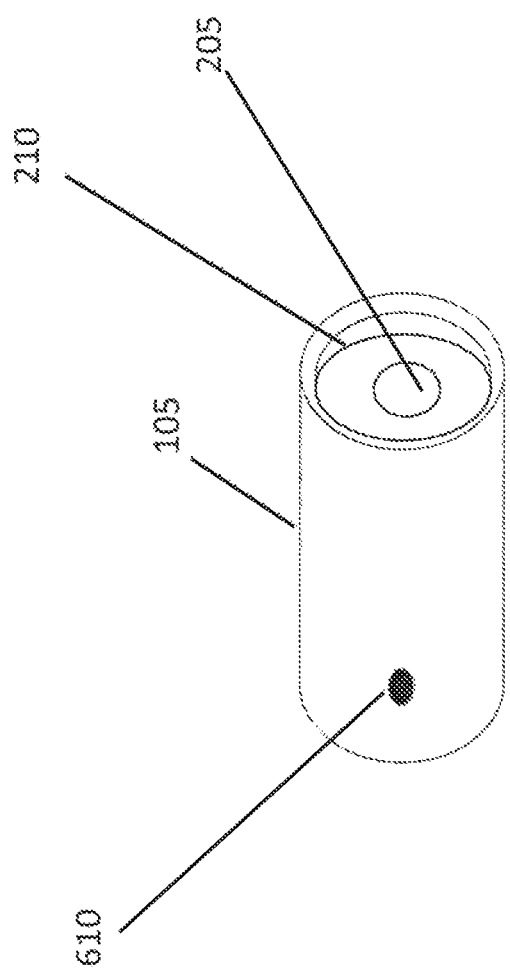
FIG. 8 illustrates a side perspective view of a casing in a spring injector in accordance with an embodiment of the invention, the size and length of which is not drawn to scale.

FIG. 8 illustrates a perspective view of a casing 105 of a spring injector in accordance with an embodiment of the invention. In FIG. 8, casing 105 is substantially cylindrical shaped. However, casing 105 may be various other volumetric shapes in accordance with various other embodiments of the invention. Casing 105 includes a nib 610 that extends out of the sidewall of the casing 105. Nib 610 is received in groove 325 of rotating portion 122 of covering 120 to restrict the rotation of portion 122 to be between the locked and unlocked positions. In accordance with some embodiments of the invention, nib 610 may be an end of pin 710 that extends through casing 105 to cooperate with trigger 130.

Casing 105 also includes recessed coupling 205 that surrounds opening 210 and has a mechanism for coupling to an ampule. For example, the recessed coupling 205 can embody female threads. In accordance with the shown embodiment, recessed coupling 205 can be formed at an end of the casing 105 and can have threads for threading or receiving male threads on an end of an ampule to couple the ampule to the spring injector 100. In accordance some various other embodiments, other coupling mechanisms may be used. A shaft from a plunger in the ampule may extend through opening 205 into cavity 110 to engage piston 216. An example of an ampule is described below with respect to FIG. 10.

Although a casing of a needleless injector in accordance with some embodiments of the invention is described with reference to FIG. 8, other bodies that are configured in other manners that add, combine, modify, and/or remove the described embodiments based upon the configurations of needleless injectors are possible.

Figure 9:
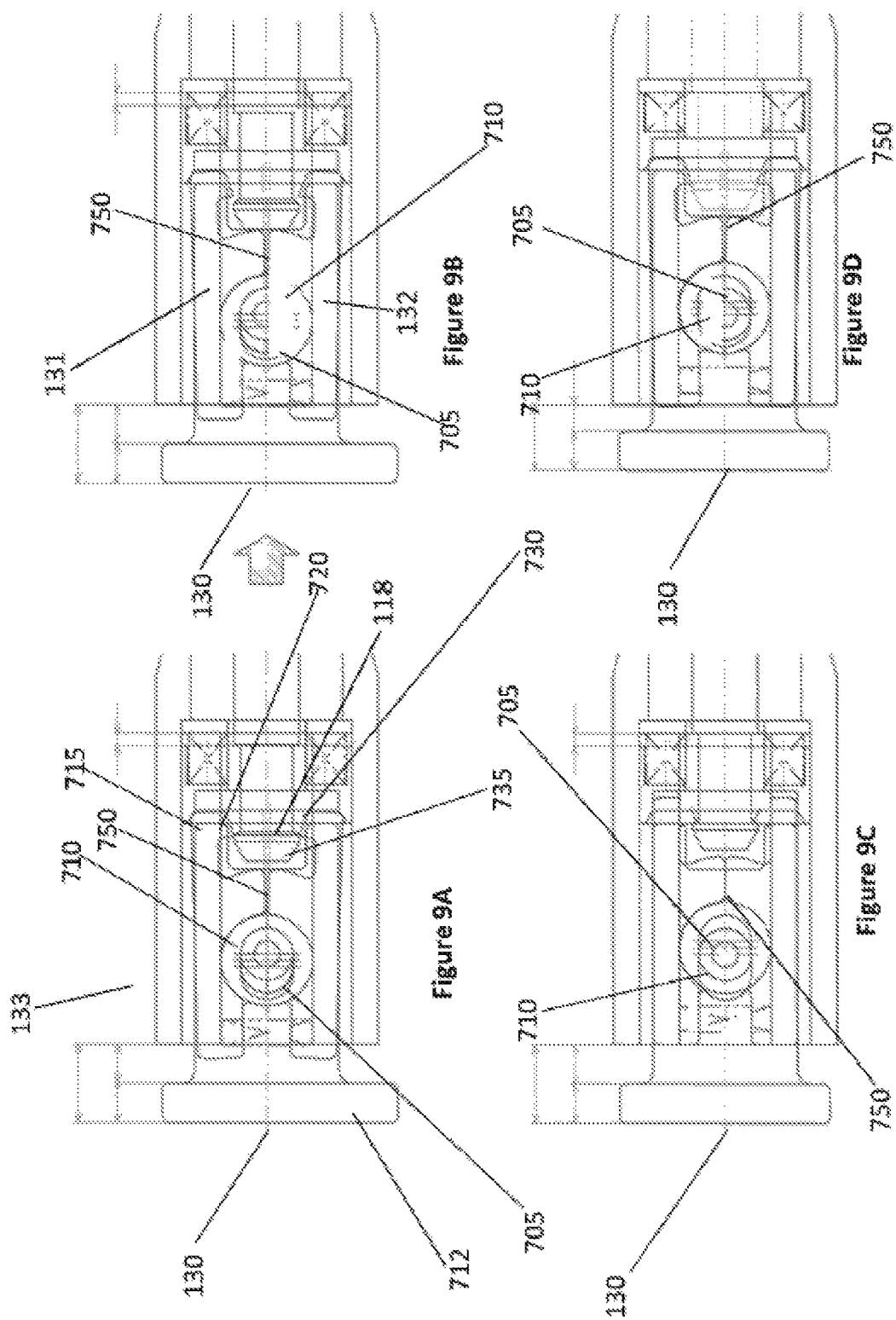
FIGS. 9A-9D illustrate cross sectional detailed views of a trigger installed into a casing of a spring injector at various positions in accordance with an embodiment of the invention.

FIGS. 9A-9D are a cross-sectional close-up views of the trigger 130 and the latch body 118 in accordance with an embodiment of the invention. As shown in FIG. 9A, trigger 130 includes a base that has a top surface. The top surface has an elongated portion 712 that extends out of the base over the outward facing surface of the covering to form an overhang over the covering. The overhang formed by elongated portion 712 engages the nib of the safety when the safety is in the locked position to restrict the movement of trigger 130 into cavity 110 of housing 102. Trigger 130 also has a portion of the top surface that does not extend out over the outward facing surface of the covering. When this portion is over the nib of the covering that is in the unlocked position, the nib does not hinder the motion of trigger 130 into the cavity and trigger 130 is free to move towards the housing when the nib is in the unlocked position.

Trigger 130 also has an opening 705 defined through the base. The opening is of sufficient length along the longitudinal axis of the housing to allow movement of trigger 130 between the ready and action positions. A pin 710 affixed at both ends to an inner surface of the cavity extends through opening 705 and restricts the movement of trigger 130 to the length of opening 705 to restrict the movement of trigger 130 to being between the ready and action positions.

As shown in FIGS. 9A-9D, pin 710 starts at an end of the opening that is proximate the cavity when trigger 130 is in the ready position. As trigger 130 is pushed inward to the cavity, the relative location of pin 710 in opening 705 moves from the proximate end of the opening to an end of the opening distal from the cavity as shown in FIGS. 9A-9D. Said differently, the pin moves from a first position within the opening 705 to a second position within the opening 705 when the trigger 130 is pressed. Pin 710 is shaped such that it pushes against the sidewalls of opening 705 forcing the portions of prongs 131, 132, apart from one another. Pin 710 then restricts the movement of trigger 130 into the cavity when trigger 130 has reached the firing position. In an example, relative sizes between the opening 705 and the portion of the pin 710 that is located in the opening causes the pin to push against the sidewalls of the opening as the pin moves first the first position to the second position with the opening.

Returning to FIG. 9A, trigger 130 includes prongs 131 and 132 (FIGS. 1, 2, and 9B). Each prong has a retaining member 715 with a hook end 720. There is split 750 between opposing portions of the prongs 131, 132, that passes through the opening 705. This split allows the two prong 131, 132 to move away from one another when activated by the pin 710 so that distal ends of the two prongs can separate to release the end cap 735 of the plunger in response to a force applied by pin 710.

In an example, pin 710 is shaped such that pin 710 pushes against side walls of the opening 705 forcing opposing portions of the prongs apart as the trigger travels into cavity 110. The opening 705 can therefore be viewed as two cut-outs, one on each of the two prongs 131, 132, such as that when aligned side-by-side, the two cut-outs define the opening 705 having the split 750 in communication with the opening. The spreading of the portions of prongs 131, 132 into the action position causes the retaining members of the prongs to release the latch body 118. In addition, an inward facing surface 720 of each retaining member may slope outwards from a bottom surface of end cap 735 of latching body 118 towards the sides of the cavity. The sloping of the retaining members may facilitate the release of the end cap 735 by the trigger allowing the latching body to move from a locked to a firing position.

An end cap 735 can be viewed as a nib extending outward from latching body 118, which can be located at an end of the shaft 117 of the piston 115. The nib has a top surface, a bottom surface and a sidewall between the top and bottom surfaces. The top surface has ends that extend outward from latching body 118 to define an overhang that extends beyond the bottom surface of the body and a sidewall of the nib. In the shown embodiment, the sidewall slopes outward from a top end proximate a center of the top surface to a bottom end proximate the ends of the overhang.

The overhang is engaged by the retaining members of the prongs to hold latching body 218 in place when the trigger is in the ready position. The sloping aids of the sidewalls of the end cap may aid in preventing the retaining members 715 from hindering the movement of latching body 118 when the body is released. In accordance with some embodiments, the side wall 730 of the latching body 118 under the overhang of endcap 735 is also sloped outward in a similar manner to the sidewall of end cap 735. In the shown embodiment, the sloping sidewall 730 of the nib engages the sloped surface of the retaining members 715 of the prongs to aid in forcing the prongs apart as trigger 130 moves from the ready position to the action position to release the end cap 735 as seen in FIGS. 9A-9D.

FIG. 10 illustrates a side perspective view of an exemplary ampule 800 that may be inserted into a spring injector in accordance with an embodiment of the invention. In FIG. 10, ampule 800 includes a housing or barrel 805 enclosing a reservoir for holding liquid medicament. A first end of housing 800 has a nozzle opening 810 defined through the surface to the reservoir. The opening is sized and shaped to provide a desired fluid velocity and pressure for causing the liquid medicament to have a desired force to perform a needleless injection when expelled using the force provided by the needleless injector.

A second side 815 of housing 805 proximate a second end has threading or is a coupling end 815 having threads or other engagement means for connecting to the spring injector. As shown, the threaded end is configured for threading in the recessed coupling of a housing of an injector. The second end of the housing 800 has an opening that is sized to a allow plunger 820 to extend into the opening. The plunger 820 has a shaft that is extendible out of the second opening and into the cavity of the housing to engage the piston such that when the piston is moved by a de-compressing spring, plunger 820 is driven into the reservoir in housing 805 to expel the liquid medicament out of nozzle opening 810. A plunger tip 820 is coupled to the plunger and in dynamic sealing arrangement with the interior surface of the housing 805.

A needleless injector configured in the manner described above can operate in the following manner. At the start of the process, the spring is in an uncompressed state inside the spring injector and an ampule is not affixed to the housing of the spring injector. As such, the shaft of in the casing of the housing of the spring injector is in the unloaded position with the shaft protruding out of the injector end of the cover. This allows the pin of the rotating portion of the casing to extend into the bore in the stable portion of the casing holding the rotating portion in the locked position. In the locked position, the nib on the rotating portion of the covering is under the overhang of the trigger to restrict the movement of the trigger into the cavity.

The spring injector may then undergoes a calking or loading process. In the calking process, the piston is forced into the cavity from the injection end to the cap end of the housing. The movement of piston into the cavity compresses the spring to a desired compression. At substantially the same time, the end cap 735 of the latching body 118 is engaged by the trigger 130, such as by the two retaining members 715 of the two prongs 131, 132 (FIGS. 9A and 9B). The trigger moves to a ready position and engages the latching body to hold the latching body in the holding position. The latching body in the holding position holds the piston in place in order to hold the spring in a compressed state.

An ampule can then be inserted into the recessed coupling of the spring injector and coupled to the spring injector. The coupling of the ampule to the spring injector causes the shaft in the stable portion of the housing to move from the unloaded position to the loaded position where the second end of the shaft approximately even with the internal surface of stable portion. The movement of the shaft to the loaded position forces the pin in the rotating portion of the housing into a recessed position in a cavity in the rotating portion. With the pin in the recessed position, the rotating portion is free to rotate from the locked position to the unlocked position. Recessed position for the pin can mean that the end of the pin that is exposed has been moved inside the housing to not interference with subsequent movements of the spring injector.

The rotating portion is rotated from the locked position to the unlocked position. The rotation causes the nib on the rotating portion to move from underneath the overhang of the trigger to a position where the trigger is free to move into the cavity of the housing. The trigger may then be activated by pushing the trigger into the cavity from the ready position to the action position. The movement of the trigger into the cavity causes the opposing potions of the prongs to be forced apart releasing the nib of the latching body. The sloping sidewall of the nib may facilitate the forcing apart the portions of the prongs by forcing the retaining members outward from one another as the trigger reaches the action position.

The moving apart of the portions of the prongs, allows the nib of the latching body to be released as it moves to a firing position. With the latching body free from the prongs, the piston is free to move by the expanding spring. This causes the spring to decompress and apply energy to the piston. The applied energy forces the piston towards the injector end of the housing. As the piston is moving towards the injector end, the piston pushes the shaft of the plunger into the ampule. The plunger, in turn, pushes the liquid medicament towards the nozzle that restricts the escape of the liquid resulting in the liquid being expelled at the desired pressure.

Methods of making and of using the needleless hypodermic injector and components thereof, including spring injectors 100 and ampules, are within the scope of the present invention.

Although limited embodiments of the needleless hypodermic injector assemblies and their components have been specifically described and illustrated herein, many modifications and variations will be apparent to those skilled in the art. Further, the invention can be a subset of features or components described herein and not to be read is requiring all of the disclosed structural features to practice the invention. Accordingly, it is to be understood that the needleless hypodermic injector assemblies and their components constructed according to principles of the disclosed devices, systems, and methods may be embodied other than as specifically described herein. The disclosure is also defined in the following claims.

What is claimed is:

1. A needleless injector assembly comprising:
a spring injector comprising a housing having a first housing portion and a second housing portion defining a bore that is common to the first housing portion and the second housing portion;
a casing is located in the bore and is fixed relative to the first housing portion, but the second housing portion is rotatable relative to the casing;
a threaded receiving end at an end of the casing to threadedly receive a threaded end of an ampule;
a pin having an end projecting from the second housing portion and into an opening of the first housing portion; and
wherein the pin is retractable away from the first portion before the second housing portion is rotatable relative to the casing.

2. The needleless injector of claim 1, wherein the second housing portion is rotatable relative to the first housing portion.

3. The needleless injector of claim 2, wherein the pin is located in a bore of a base portion of the second housing portion.

4. The needleless injector of claim 1, wherein an ampule is threaded to the threaded receiving end of the casing.

5. The needleless injector of claim 1, further comprising a piston and a spring located inside the casing.

6. The needleless injector of claim 1, further comprising a trigger having a push end located externally of the second housing portion and a triggering mechanism comprising two relatively movable prongs.

7. The needleless injector of claim 5, wherein the piston comprises a piston head and a shaft having a latching body.

8. The needleless injector of claim 7, wherein a trigger having a push end located externally of the second housing portion and a triggering mechanism comprising two relatively movable prongs each comprising retaining member grips the latching body to hold the spring in a compressed state.

9. The needleless injector of claim 8, further comprising a slit and an opening formed by two cut-outs between the two prongs.

10. A method of making a needleless injector assembly comprising:
forming a spring injector comprising a housing having a first housing portion and a second housing portion defining a bore that is common to the first housing portion and the second housing portion;

placing a casing in the bore so that the casing is fixed relative to the first housing portion, but the second housing portion is rotatable relative to the casing;

providing the casing with a threaded receiving end at an end of the casing to threadedly receive a threaded end of an ampule;

placing a pin having an end projecting from the second housing portion and into an opening of the first housing portion; and wherein the pin is retractable away from the first portion before the second housing portion is rotatable to the casing.

11. The method of claim 10, further comprising placing a shaft in a bore of a base portion of the first housing portion.

12. The method of claim 11, further comprising attaching an ampule to the casing so that the ampule pushes the shaft into the pin.

13. The method of claim 12, further comprising providing a trigger having two movable prongs, a piston, and a spring and gripping the piston with the two movable prongs.

14. The method of claim 13, further comprising rotating the second housing portion relative to the first housing portion.

15. The method of claim 14, further comprising moving the trigger after the second housing portion is rotated.

* * * * *